United States Patent
Fischell et al.

(12) 
(10) Patent No.: US 6,230,049 B1
(45) Date of Patent: May 8, 2001

(54) INTEGRATED SYSTEM FOR EEG MONITORING AND ELECTRICAL STIMULATION WITH A MULTIPLICITY OF ELECTRODES

(75) Inventors: Robert E. Fischell, Dayton, MD (US); David R. Fischell, Fair Haven, NJ (US)

(73) Assignee: Neuro Pace, Inc., Sunnyvale, CA (US)

( * ) Notice: Subject to any disclaimer, the term of this patent is extended or adjusted under 35 U.S.C. 154(b) by 0 days.

(21) Appl. No.: 09/373,676

(22) Filed: Aug. 13, 1999

(51) Int. Cl.[7] ................................................. A61B 05/00
(52) U.S. Cl. .............................................................. 600/544
(58) Field of Search ...................................... 600/544, 545, 600/306

(56) References Cited

U.S. PATENT DOCUMENTS

| | | | | |
|---|---|---|---|---|
| 3,850,161 | * | 11/1974 | Liss ........................................ | 600/544 |
| 4,878,498 | * | 11/1989 | Abrams ................................. | 600/544 |
| 5,269,302 | * | 12/1993 | Swartz et al. .......................... | 607/45 |
| 5,311,876 | * | 5/1994 | Olsen et al. ........................... | 600/544 |
| 5,730,146 | * | 3/1998 | Itil et al. ............................... | 600/544 |
| 5,755,230 | * | 5/1998 | Schmidt et al. ....................... | 600/544 |
| 5,857,978 | * | 1/1999 | Hively et al. ......................... | 600/544 |
| 6,016,449 | * | 1/2000 | Fischell et al. ........................ | 607/45 |

\* cited by examiner

*Primary Examiner*—Robert L. Nasser (57) ABSTRACT

The disclosed invention is an integrated system for EEG monitoring and electrical stimulation from a multiplicity of scalp or intracranial implanted electrodes. The system integrates EEG monitoring and brain stimulation, supports remote electrode selection for stimulation and provides a wireless connection between the patient's brain electrodes and the EEG analysis workstation used to collect EEG data, analyze EEG signals and control system functionality.

42 Claims, 4 Drawing Sheets

INTEGRATED SYSTEM FOR EEG MONITORING AND ELECTRICAL STIMULATION WITH A MULTIPLICITY OF ELECTRODES

FIELD OF USE

This invention is in the field of devices for the treatment of neurological disorders in human subjects, particularly those disorders that originate in the brain.

BACKGROUND OF THE INVENTION

It is well known that, in certain patients, epileptic seizures consistently originate from a single location within the brain. When a primary epileptogenic region or seizure focus is suspected some form of monitoring by implanted electrodes may be performed during which time the electrodes are connected to recording instruments such as an electroencephalograph (EEG) machine. Additionally, in some patients, intracranial electrical stimulation using implanted electrodes is performed to map regional brain function as a precursor to surgical removal of the epileptogenic region. Current apparatus for performing such a mapping procedure requires the patient be connected to both an EEG monitoring system and a separate electrical stimulator. In addition, these systems are connected to the patient via a cumbersome multi-wire cable. Current systems also require manual connection of the electrical stimulation systems to specific electrodes (i.e. clip leads are moved on a connector box by the operator).

Having separate monitoring and stimulation systems, requires two sets of controls and complicates operation as compared to an integrated monitoring and stimulation system with a single control console.

Multi-wire cables are a source of unwanted electrical noise and place constraints on patient movement. It is highly desirable to have the EEG monitoring and stimulation system be remotely controllable from the EEG monitoring system console without direct wire connection to the patient.

SUMMARY OF THE INVENTION

The disclosed invention is an integrated system for EEG monitoring and electrical stimulation from a multiplicity of scalp or intracranial implanted electrodes. The system integrates EEG monitoring and brain stimulation, supports remote electrode selection for stimulation and provides a wireless connection between the patient's brain electrodes and the EEG analysis workstation used to collect EEG data, analyze EEG signals and control system functionality.

The EEG monitoring and electrical stimulation system comprises the EEG analysis workstation, a patient electronics module wired to a multiplicity of electrodes, and a wireless data link between the EEG analysis workstation and the patient electronics module. The patient electronics module includes multi-channel low noise amplifiers, analog-to-digital (A to D) converters and a programmable electrical stimulator with selectable output electrodes.

The EEG analysis workstation has the capability to process, store, retrieve and display patient EEG data. The EEG analysis workstation also has the capability to program and control the electrical stimulator in the patient electronics module. It is also envisioned that high, low and band pass filters are part of the amplifier system in the patient electronics module and that they are programmable from commands sent by the EEG analysis workstation via the wireless data link to the patient electronics module.

To use the integrated EEG analysis and stimulation system for a standard EEG monitoring and brain mapping procedure, a neurosurgeon would first implant a multiplicity of brain electrodes under the patient's scalp. Brain electrodes can include an array of surface electrodes placed above the surface of the patient's brain and/or a multiplicity of depth electrodes implanted deep into the patient's brain. Intracerebral depth electrodes, which are often line arrays of electrodes, are useful for recording from or stimulating deep cerebral structures such as the amygdala, hippocampus, cingulate and orbital-frontal regions which deep cerebral structures are characteristically involved in many medically refractory partial epilepsies. Brain electrodes can also include electrodes placed elsewhere under the patient's scalp near or within the brain.

The patient electronics module is then attached to the brain electrodes and turned on. The EEG analysis workstation is then activated and the system's wireless link is checked. If all is working, the system is ready to collect EEG data from the patient's brain electrodes. After collecting and displaying the EEG data using the EEG analysis workstation, the physician can then map the function of the brain tissue near each of the brain electrodes by electrical stimulation of a specific subset of electrodes; the specific subset of electrodes being selectable from the EEG analysis workstation.

In another application, the integrated EEG analysis and stimulation system can be used to test the efficacy of responsive stimulation for the control of epileptogenic activity (i.e., to abort an epileptic seizure). In this case, there is an additional step of activating the stimulator in the patient electronics module when a seizure or seizure-like discharges are detected by the EEG analysis system. For this purpose, programmable detection algorithms for detecting specific types of epileptiform activity would be an essential part of the EEG analysis workstation software. The integrated EEG monitoring and electrical stimulation system would be programmed to determine specific therapeutic stimulation parameters during an evaluation procedure prior to the implantation of an electrical stimulation therapy device (a neuropacemaker). Such an evaluation procedure would be especially useful for determining the seizure detection and stimulation parameters for a closed-loop neuropacemaker that is responsive to the onset of epileptic seizures. A neuropacemaker such as this is described in U.S. patent application Ser. No. 8/957,869 by Fischell et al.

Thus it is an object of the present invention to have an integrated EEG monitoring and electrical stimulation system that has a wireless link between a patient electronics module and an EEG analysis workstation.

Another object of the present invention is to have an integrated EEG monitoring and electrical stimulation system that allows choice of electrodes for stimulation from the EEG monitoring system console.

Still another object of the present invention is to have an integrated patient electronics module, which contains both multi-channel EEG amplification means and electrical stimulation means.

Yet another object of the present invention is to have an EEG analysis workstation capable of automated detection of epileptiform activity using EEG signals received from a patient electronics module by means of a wireless data link.

Yet another object of the present invention is to have an EEG monitoring system with a wireless link to a patient electronics module attached to brain electrodes.

Yet another object of the present invention is to have an EEG analysis workstation capable of (1) automated detection of epileptiform activity, and (2) responsive stimulation to attempt to control or abort the epileptiform activity; the epileptiform signals being received and the stimulation being applied from a remote patient electronics module using a wireless link.

These and other objects and advantages of this invention will become obvious to a person of ordinary skill in this art upon reading of the detailed description of this invention including the associated drawings as presented herein.

DETAILED DESCRIPTION OF THE DRAWINGS

Figure 1:
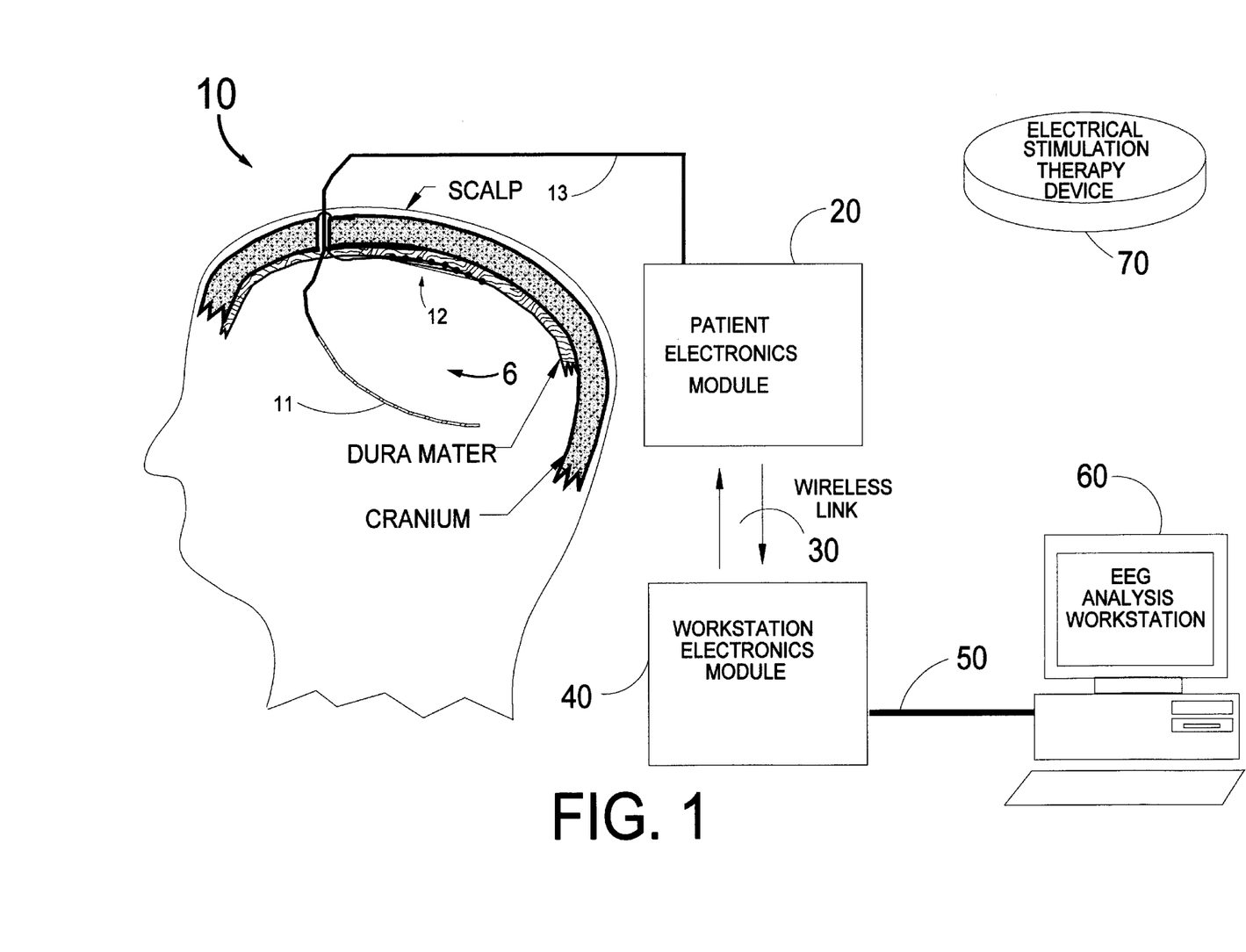
FIG. 1 is a block diagram of the present invention of an integrated system for EEG monitoring and electrical stimulation system with a multiplicity of brain electrodes.

FIG. 1 is a block diagram of the integrated EEG monitoring and stimulation system 10 used for the detection and analysis of epileptiform activity from implanted brain electrodes 6. The integrated EEG monitoring and stimulation system 10 also provides the capability to selectively apply electrical stimulation to any one or more of the brain electrodes 6.

Brain electrodes 6 include both the depth electrodes 11 and surface electrodes 12 and may also include electrodes placed elsewhere under or onto the patient's scalp near or within the brain. A multiplicity of depth electrodes 1 is implanted deep into the patient's brain. Intracerebral depth electrodes 11, which are often line arrays of electrodes, are useful for recording from or stimulating deep cerebral structures such as the amygdala, hippocampus, cingulate and orbital-frontal regions which deep cerebral structures are characteristically involved in many medically refractory partial epilepsies. An array of surface electrodes 12 is placed typically on the surface of the patient's brain and may include more than 100 separate electrodes.

A multiple conductor electrode cable 13 connects the depth electrodes 11 and surface electrodes 12 to a patient electronics module 20. The patient electronics module 20 amplifies the EEG signals from the brain electrodes 6 and transmits the EEG data from the multiple brain electrodes 6 over a wireless link 30 to the workstation electronics module 40. The patient electronics module 20 also includes the capability to selectively provide electrical stimulation to any one or more of the individual brain electrodes that collectively form the brain electrodes 6. The workstation electronics module 40 has a hard-wired data connection 50 to the EEG analysis workstation 60.

The EEG analysis workstation 60 is envisioned as a standard desktop computer running software designed to process, store, play back and display on a monitor the patient's EEG signals received over the wireless data link 30 and the hard-wired data connection 50 from the workstation electronics module 40. In addition, the EEG analysis workstation 60 has built-in algorithms for real-time processing and detection of epileptiform activity received through the workstation electronics module 40 from the patient electronics module 20. The EEG analysis workstation 60 also has the capability to send programming and commands over the data connection 50 to the workstation electronics module 40 that the workstation electronics module 40 then transmits over the wireless link 30 to the patient electronics module 20.

The commands sent from the EEG analysis workstation 60 include the command to start and stop electrical stimulation of a selected set of the brain electrodes 6 by means of the patient electronics module 20. The programming sent from the EEG analysis workstation 60 further includes the settings for amplifier gain, high, low and band pass filter and the signal parameters for the electrical stimulation.

For the detection and mapping procedure, the integrated EEG analysis and stimulation system 10 would be typically used as follows:

1. Brain electrodes 6 including surface electrodes 12 and/or depth electrodes 11 would be implanted by a neurosurgeon.
2. EEG data would be collected by the EEG analysis workstation 60 from EEG signals amplified by the patient electronics module 20, transmitted by the patient electronics module 20 over the wireless link 30 to the workstation electronics module 40 which in turn sends the signals over the data connection 50 to the EEG analysis workstation 60.
3. After sufficient epileptiform activity has been collected by the EEG analysis workstation 60, a physician would use the stored EEG data displayed on the EEG analysis workstation to select appropriate brain electrodes 6 for the stimulation phase of the mapping procedure. The appropriate electrodes would probably be those in the region that shows the highest indication of epileptiform activity.
4. The stimulation parameters (e.g., pulse width, voltage, pulse frequency, etc.) would then be selected on the EEG analysis workstation 60 and transmitted through the workstation electronics module 40 to the patient electronics module 20 via the wireless link 30.
5. The commands to start and stop stimulation on specific brain electrodes 6 would then be transmitted through the workstation electronics module 40 to the patient electronics module 20 from the EEG analysis workstation 60 via the wireless link 30.
6. The stimulation effects on the patient would be noted by the physician as in a standard brain mapping procedure. This standard brain mapping procedure uses electrodes near the site of the epileptic focus to map brain function as a precursor to surgical excision of the epileptogenic region.

The integrated EEG analysis and stimulation system 10 is also ideally suited for use with an epileptiform activity detection and control procedure to identify patients who are a candidate for implantation of an electrical stimulation therapy device 70 to control epileptiform activity. The electrical stimulation therapy device 70 would typically be a closed-loop, responsive neuropacemaker that would stimulate a specific region in response to detected epileptiform activity. It is also envisioned that a continuous stimulation neuropacemaker could be implanted if continuous stimulation from the EEG monitoring and electrical stimulation system 10 shows a reduction in epileptiform activity.

For an epileptiform activity detection and control procedure the integrated EEG analysis and stimulation system 10 would be used as follows:

1. Brain electrodes 6 including surface electrodes 12 and/or depth electrodes 11 would be implanted by a neurosurgeon.

2. EEG data would be collected by the EEG analysis workstation 60 from EEG signals amplified by patient electronics module 20, transmitted by the patient electronics module 20 over the wireless link 30 to the workstation electronics module 40 which in turn sends the signals over the data connection 50 to the EEG analysis workstation 60.
3. After sufficient epileptiform activity has been collected by the EEG analysis workstation 60, a physician would use the stored EEG data displayed on the EEG analysis workstation 60 to select an appropriate set of the brain electrodes 6 for the stimulation phase of the epileptiform activity detection and control procedure. An analysis of the stored EEG data would be used to program the epileptiform activity detection algorithms built into the EEG analysis workstation 60.
4. Commands to start and stop electrical stimulation to the appropriate set of the brain electrodes 6 are then sent by the physician from the EEG analysis workstation 60. The goal is to induce epileptiform activity that may include after-discharges from the epileptogenic region of the patient's brain. These after-discharges are typically similar to natural epileptiform activity. Inducing after-discharges may require empirical testing of various stimulation parameters programmed from the EEG analysis workstation 60 through the workstation electronics module 40 to the patient electronics module 20.
5. When induced epileptiform activity occurs, the physician will then use the EEG analysis workstation 60 to initiate stimulation that is identical to the stimulation that caused the after-discharge activity in step 4. If the epileptiform activity is stopped as compared with epileptiform activity where no second stimulation is applied, go to step 7.
6. If the epileptiform activity is not stopped, adjust the stimulation parameters using the EEG analysis workstation 60 until the epileptiform activity is stopped, then go to step 7. Typically, the choice of electrodes, electrical stimulation voltage and/or pulse width would be adjusted until induced epileptiform activity is promptly stopped. If the epileptiform activity cannot be stopped, then the patient may not be a candidate for electrical stimulation therapy.
7. Retain the information on stimulation parameters and the specific set of selected electrodes for use in connecting and programming the electrical stimulation therapy device 70.
8. It is also envisioned that an automated system could then be used to detect natural epileptiform activity and automatically respond rather than having the reapplication of stimulation done manually by the physician through the EEG analysis workstation 60. If a patient has natural seizures every few hours, this is easy to accomplish. On the other hand, if the patient has only one seizure per week, it would probably not be practical to wait for the occurrence of natural seizures.
9. Replace the patient electronics module 20 with the electrical stimulation therapy device 70, which has been programmed with the detection and stimulation parameters, identified by the EEG analysis workstation 60 from steps 1 through 8. A test could then be conducted for automated responsive detection and stimulation using the electrical stimulation therapy device 70 attached outside of the patient's body.
10. Make minor adjustments to the programming of the electrical stimulation therapy device 70 if necessary to optimize efficacy.
11. The neurosurgeon then could complete the permanent implantation of the electrical stimulation therapy device 70 with appropriately placed brain electrodes 6 for detection and stimulation.

It is also envisioned that the electrical stimulation therapy device 70 could be an external device used with implanted brain electrodes 6, although a permanently implanted electrical stimulation therapy device 70 is the preferred embodiment. It is also envisioned that the electrical stimulation therapy device 70 could be implanted in a hole created by removal of a section of the cranium.

The wireless link 30 may employ radiofrequency (RF) or infrared (IR) technology, both of which are well known wireless communication technologies. The data connection 50 would be hard-wired and would utilize a standard computer interface such as a PC serial or parallel port connection, a Universal Serial Bus (USB) port or a high speed Small Computer System Interface (SCSI) connection. It is also envisioned that the workstation electronics module 40 might be a circuit card inserted into the ISA or PCI bus card slots in the EEG analysis workstation 60 with the data connection 50 being the ISA or PCI bus itself.

Figure 2:
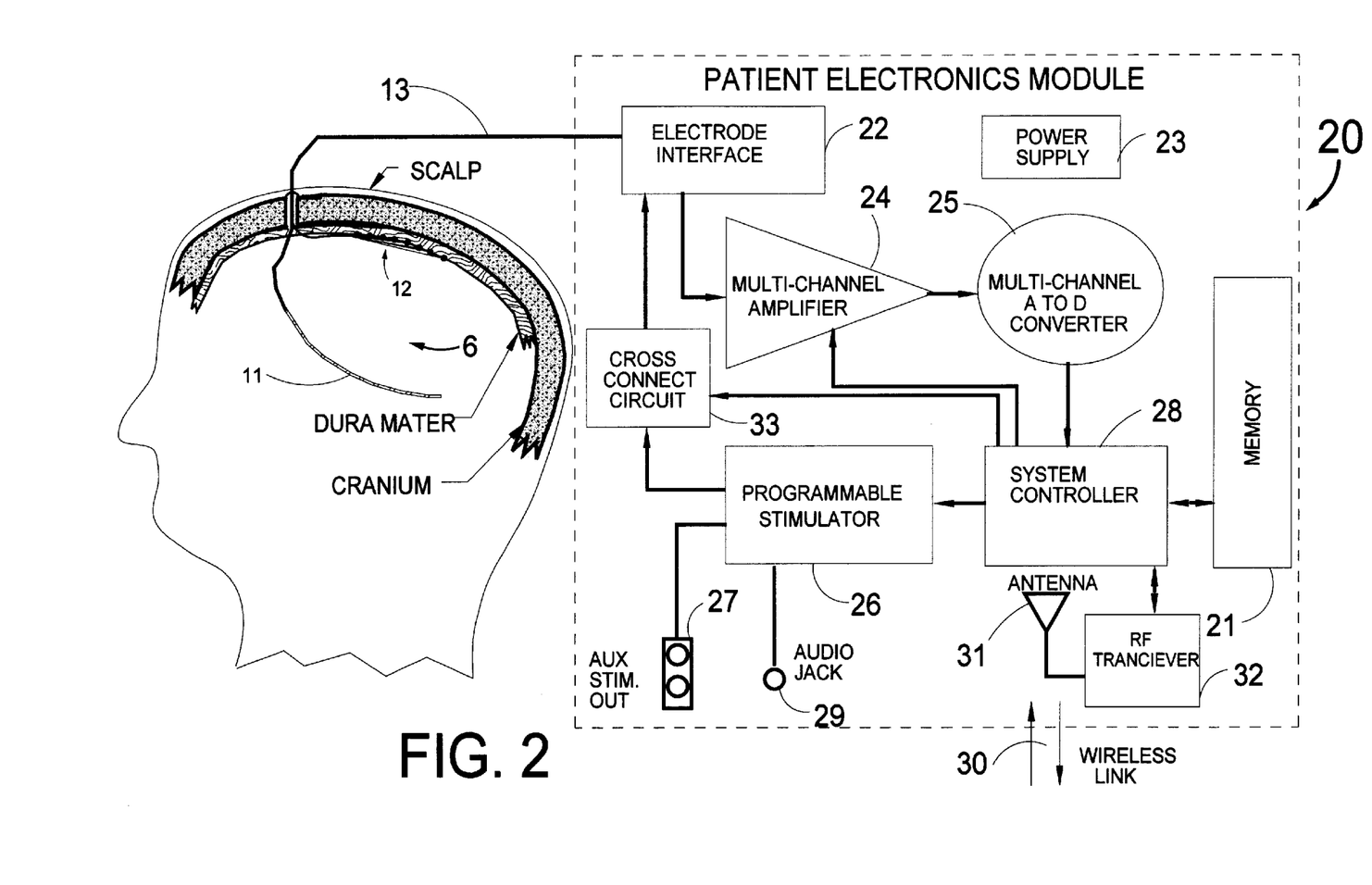
FIG. 2 is a block diagram of the patient electronics module of the integrated EEG analysis and stimulation system.

FIG. 2 includes a block diagram of the patient electronics module 20 of the integrated EEG analysis and stimulation system 10 shown in FIG. 1. The major components of the patient electronics module 20 are an electrode interface 22, power supply 23, multi-channel amplifier 24, multi-channel analog-to-digital (A to D) converter 25, programmable, electrical stimulator 26, cross connect circuit 33, system controller 28 and RF transceiver 32 with antenna 31. The electrode interface 22 has connectors to terminate the multiple conductors of the electrode cable 13 from the brain electrodes 6. The electrode interface 22 provides connectivity to the multi-channel amplifier 24 for incoming EEG signals from the brain electrodes 6 and connectivity to the brain electrodes 6 from the programmable electrical stimulator 26.

The cross connect circuit 33 is used to switch the output of the programmable electrical stimulator 26 to a specific subset of the brain electrodes 6 terminated by the electrode interface 22. The electrodes to be used for stimulation are selectable by commands from the system controller 28 to the cross connect circuit 33.

The multi-channel amplifier 24 has the capability to amplify the EEG signals from each of the brain electrodes 6, as well as to provide high, low and band pass filtering of the EEG signals. The filter parameters for the multi-channel amplifier 24 are received by the multi-channel amplifier 24 from the system controller 28. The amplified and filtered EEG signals from the multi-channel amplifier 22 are converted to digital format by the multi-channel analog-to-digital converter 25.

The multi-channel analog-to-digital converter 25 outputs the digital data stream to the system controller 28 for storage in the memory 21 and/or wireless transmission from the RF transceiver 32 with antenna 31 via the wireless link 30 to the workstation electronics module 40 seen in FIG. The system controller 28 also receives from the workstation electronics module 40 incoming commands and programming through the RF transceiver 32 with antenna 31 via the wireless link 30.

It is envisioned that the digital memory 21 could be capable of storing as much as 2 days of EEG signals from as many as 128 channels or a 8 days of data from 32 channels. Flash memory currently used for digital camera film may be the preferred type of memory to use. Digital compression by the system controller 28 of the signals from the analog-to-digital converter 25 may be used to reduce the amount of memory 21 needed or allow for greater storage.

The programming received by the system controller 28 is also stored in the digital memory 21. The commands and programming received include commands to the cross connect circuit 33 to specify the subset of the brain electrodes 6 for stimulation, filter settings for the multi-channel amplifier 24 and stimulation parameters for the programmable electrical stimulator 26.

The digital memory 21 can also be used to store digital EEG data from as many as 32 brain electrodes for later transmission through the wireless link 30. To facilitate storage, the EEG data from the multi-channel A to D converter 25 could be compressed by the system controller 28 before storage in the digital memory 21. By using the digital memory 21 for EEG recording, the patient electronics module 20 becomes an excellent device for ambulatory patient EEG monitoring.

The programmable electrical stimulator 26 also has an auxiliary stimulation output connector 27 to allow attachment to external electrodes (not shown) that may be used to provide electrical stimulation to the patient's skin. Such external stimulation has been shown in some cases to be effective in controlling epileptiform activity. An audio output jack 29 from the programmable electrical stimulator 26 allows the patient electronics module 20 to provide a sound to the patient either to notify the patient that a seizure has occurred or to attempt to stop the epileptiform activity by an auditory stimulus. The audio output jack 29 would typically be a standard stereo jack to allow easy connection to a loudspeaker or a set of headphones. It is also envisioned that either the auxiliary stimulation output connector 27 or the audio output jack 29 could be used to trigger other sensory stimulus to the patient such as a mechanical vibrator or a flashing light.

The power supply 23 should be a rechargeable or replaceable battery with appropriate voltage regulators and/or d-c to d-c conversion to drive the circuitry of the patient electronics module 20.

Figure 3:
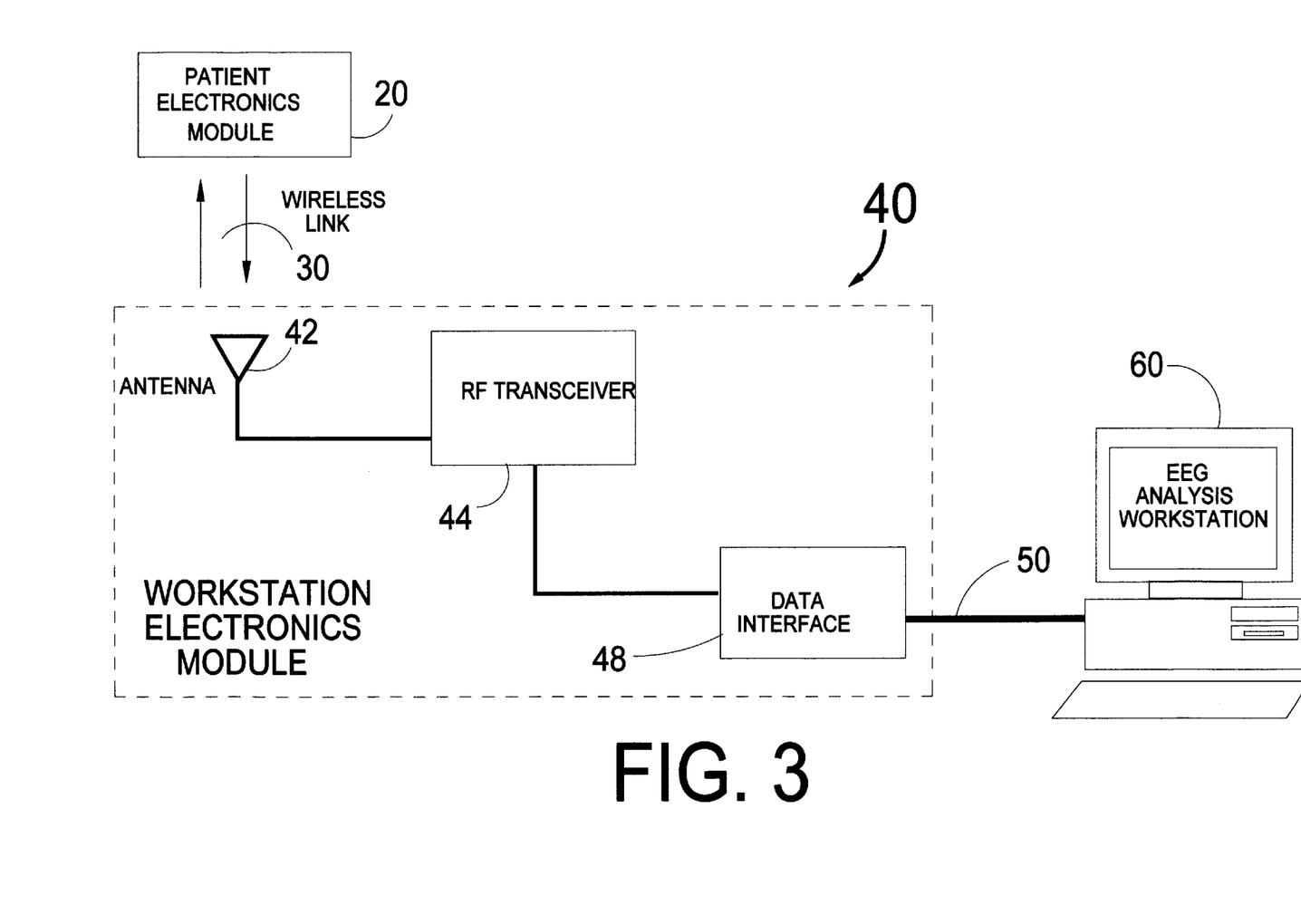
FIG. 3 is a block diagram of the workstation electronics module of the integrated EEG analysis and stimulation system.

FIG. 3 is a block diagram of the workstation electronics module 40 of the integrated EEG analysis and stimulation system 10 shown in FIG. 1. The workstation electronics module 40 comprises an antenna 42 and RF transceiver 44 which provide bidirectional data communication through the wireless link 30 to the patient electronics module 20. A data interface 48 provides the means for the EEG analysis workstation 60 to send and receive commands and data from the RF transceiver 44 over the data connection 50.

RF transceiver chip sets such as those used for 900 GHz wireless phones or next generation standards such as Bluetooth are well known. Circuits to provide standard data interfaces such as serial, parallel and USB connections to a personal computer are well known. It is also envisioned that infrared transmitters and receivers such as those used in television remote controls or the infrared communications (IRDA) port on laptop computers could be used to provide the wireless link 30. If infrared technology were used, the antenna 42 would be replaced by the combination of an LED and a photodiode, as would the antenna 31 of FIG. 2. Radiofrequency wireless technology is the preferred technology as the system could function well with the patient in any position within 50 feet of the workstation electronics module 40. Although infrared technology is less prone to electrical noise, its use could limit the patient's mobility and the distance of the patient from the workstation electronics module 40.

Commercially available EEG workstations are available that provide real time display of multi-channel EEG data, storage and retrieval of EEG data and limited data processing of the EEG data. The EEG analysis workstation 60 of the present invention would perform much the same tasks as such a commercially available EEG workstation with the following additional capabilities:

1. Real-time epileptiform activity detection algorithms.
2. The ability to run two or more real-time epileptiform activity detection algorithms concurrently.
3. The ability to create patient specific templates to be used in epileptiform activity detection algorithms.
4. A control function to allow an operator to control electrical stimulation from the patient electronics module 20.
5. A programming function to download the electrical stimulation parameters to the patient electronics module 20.
6. The capability for automatically responding to a detected seizure by triggering electrical stimulation from the patient electronics module 20 to abort an epileptic seizure.
7. The capability to download programming into an implantable stimulation therapy device 70.

Figure 4:
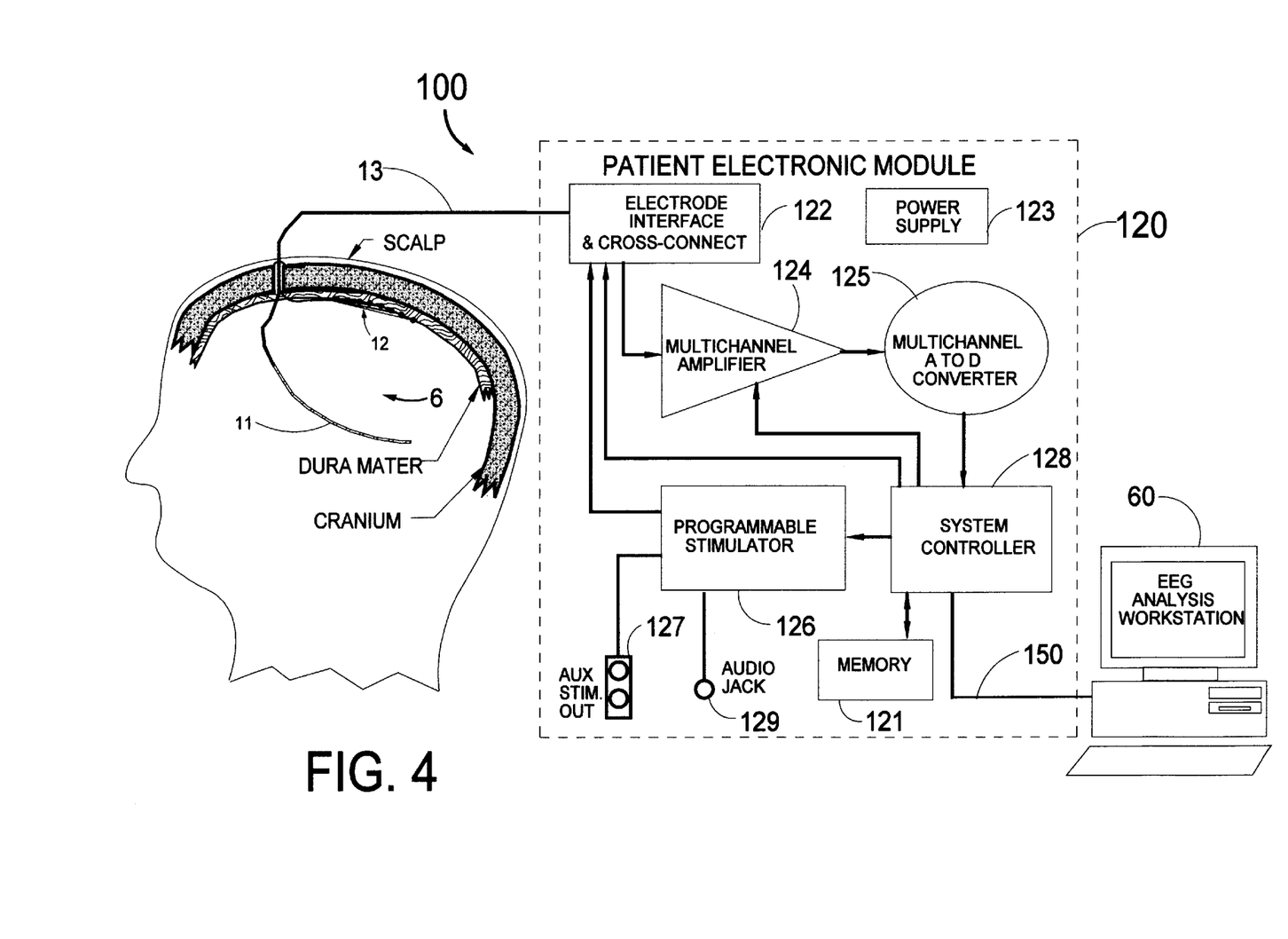
FIG. 4 is a block diagram of an alternate embodiment of the present invention integrated EEG analysis and stimulation system for detection from and stimulation of brain electrodes.

FIG. 4 is a block diagram of an alternative embodiment of the present invention consisting of an integrated EEG analysis and stimulation system 100 for detection of epileptiform activity from and electrical stimulation of brain electrodes 6. The integrated EEG analysis and stimulation system 100 differs from the integrated EEG analysis and stimulation system 10 of FIG. 1 in that the patient electronics module 120 is hard wired to the EEG analysis workstation 60 by means of the data connection 150.

The patient electronics module 120 of FIG. 4 comprises an electrode interface & cross-connect 122, power supply 123, multi-channel amplifier 124, multi-channel analog-to-digital converter 125, programmable electrical stimulator 126, system controller data interface 128, and memory 121. The electrode interface and cross-connect 122 has connectors to terminate the multiple conductors of the electrode cable 13 from the brain electrodes 6. The electrode interface and cross-connect 122 also has the capability to switch the output of the programmable electrical stimulator 126 to a specified subset of the brain electrodes 6 as a result of commands from the system controller 128.

The electrode interface 122 is connected to the multi-channel amplifier 124 to receive EEG signals from the brain electrodes 6. The programmable electrical stimulator 126 sends stimulation signals to the brain electrodes 6 via the electrode interface and cross-connect 122. The multi-channel amplifier 124 has the capability to amplify the EEG signals from the brain electrodes 6 as well as provide high, low and band pass filtering of EEG signals. The filter parameters for the multi-channel amplifier 124 (such as the cut-off frequency of a low-pass filter) are received by the multi-channel amplifier 124 from the system controller 128. The amplified and filtered EEG signals from the multi-channel amplifier 124 are converted to digital data by the multi-channel, analog-to-digital converter 125 which outputs the digital data stream to the system controller 128 for transmission over the hard-wired data connection 150 to the EEG analysis workstation 60. The system controller 128 also receives incoming commands and programming from the EEG analysis workstation 60 via the data connection 150. The commands and programming received include commands to provide stimulation onto specific brain electrodes 6, commands to set filter settings for the multi-channel amplifier 124 and stimulation parameters for the programmable electrical stimulator 126. The programming is stored by the system controller 128 in the memory 121.

The programmable electrical stimulator 126 also has an auxiliary stimulation output connector 127 to allow attachment for external electrodes (not shown) that may be used to provide electrical stimulation to the patient's skin. Such external stimulation has been shown in some cases to be effective in controlling epileptiform activity. An audio out jack 129 from the programmable electrical stimulator 126 allows the patient electronics module 120 to provide a sound to the patient either to notify the patient that a seizure has occurred or to attempt to stop the epileptiform activity by an auditory stimulus. The audio out jack 129 would typically be a standard stereo jack to allow easy connection to a loudspeaker or a set of headphones.

The power supply 123 should be a rechargeable or replaceable battery with appropriate voltage regulators and/ or a d-c to d-c converter to drive the circuitry of the patient electronics module.

It is also envisioned that the power for the patient electronics module 120 could be provided by the EEG analysis workstation 60.

Although standard terminology for the electrical signals from intracranial electrodes is electrocorticograms, EEG has been used here to refer to all electrical signals from brain electrodes including intracranial electrodes.

Various other modifications, adaptations, and alternative designs are of course possible in light of the above teachings. Therefore, it should be understood at this time that within the scope of the appended claims the invention might be practiced otherwise than as specifically described herein.

What is claimed is:

1. An integrated system for EEG monitoring and electrical stimulation, comprising:
    a multiplicity of brain electrodes having conducting means to carry electrical signals to and from the multiplicity of brain electrodes;
    an EEG analysis workstation having the capability to process, store and display EEG signals from the multiplicity of brain electrodes. The EEG analysis workstation also having the capability to initiate the electrical stimulation of a subset of the multiplicity of brain electrodes;
    a workstation electronics module connected to the EEG analysis workstation, the workstation electronics module having the capability to provide wireless data communication capability for the EEG analysis workstation.
    a patient electronics module comprising (1) an interface to the conducting means carrying the EEG signals from the multiplicity of brain electrodes, (2) a multiplicity of signal amplifiers having the capability to amplify the electrical signals carried by the conducting means from the multiplicity of brain electrodes, (3) a programmable electrical stimulator having the capability to generate electrical stimulation signals to be carried by the conducting means to a subset of the multiplicity of brain electrodes, and (4) wireless data communication means having the capability to send and receive data to and from the workstation electronics module.

2. The system of claim 1 wherein the EEG analysis workstation further comprises seizure detection means for identifying epileptiform activity from the brain electrodes.

3. The system of claim 2 wherein the EEG analysis workstation has the capability to automatically initiate electrical stimulation to the brain electrodes when epileptiform activity is detected by the seizure detection means.

4. The system of claim 2 wherein the seizure detection means comprises two or more detection algorithms that may be used concurrently to identify epileptiform activity.

5. The system of claim 1 wherein the patient electronics module further comprises an audio output jack for connecting an auditory stimulus device to the patient electronics module.

6. The system of claim 5 wherein the auditory stimulus device is a set of headphones.

7. The system of claim 5 wherein the auditory stimulus device is a loudspeaker.

8. The system of claim 1 wherein the patient electronics module further comprises an auxiliary stimulator interface for connecting additional stimulation devices to the patient electronics module.

9. The system of claim 1 wherein the wireless data communication means is a radiofrequency electromagnetic wave signal.

10. The system of claim 1 wherein the wireless data communication means is an infrared signal.

11. The system of claim 1 wherein the multi-channel amplifier has the additional capability to provide low pass filtering of EEG signals.

12. The system of claim 1 wherein the multi-channel amplifier has the additional capability to provide high pass filtering of EEG signals.

13. The system of claim 1 wherein the multi-channel amplifier has the additional capability to provide band pass filtering of EEG signals.

14. The system of claim 1 wherein the patient electronics module is battery powered.

15. The system of claim 1 wherein the subset of the multiplicity of brain electrodes used for stimulation is controlled by commands from the EEG analysis workstation.

16. A portable patient's apparatus for EEG monitoring and electrical stimulation, comprising:
    a multiplicity of brain electrodes having electrical conducting means to carry electrical signals to and from the multiplicity of brain electrodes; a subset of the multiplicity of brain electrodes with conducting means being used for the purpose of electrical stimulation of the brain,
    a patient electronics module comprising (1) an interface to the conducting means carrying the EEG signals from the multiplicity of brain electrodes, (2) a multiplicity of signal amplifiers having the capability to amplify the electrical signals carried by the conducting means from the multiplicity of brain electrodes, (3) a programmable electrical stimulator having the capability to generate electrical stimulation signals carried by the conducting means to the subset of the multiplicity of brain electrodes and (4) a battery power supply to allow the patient electronics module to be portable so as not to constrain the patient's movement.

17. The patient electronics module of claim 16 further comprising a cross-connect circuit capable of switching the electrical stimulation signals generated by the programmable electrical stimulator to select the specific subset of the multiplicity of brain electrodes to be used for electrical stimulation.

18. The system of claim 17 further comprising a system controller with the capability to transmit programming instructions and commands to the signal amplifiers, programmable electrical stimulator and cross-connect circuit.

19. The system of claim 16 further comprising analog-to-digital conversion circuitry capable of converting the outputs of the multiplicity of signal amplifiers into digitized EEG signals.

20. The system of claim 19 further comprising digital memory circuits capable of storing the digitized EEG signals.

21. The system of claim 16 further comprising external equipment and communication means to send and receive signals to and from the external equipment.

22. The system of claim 21 wherein the communication means sends and receives signals from the external equipment via a wireless link.

23. The apparatus of claim 16 wherein the multi-channel amplifier has the additional capability to provide low pass filtering of EEG signals.

24. The apparatus of claim 16 wherein the multi-channel amplifier has the additional capability to provide high pass filtering of EEG signals.

25. The apparatus of claim 16 wherein the multi-channel amplifier has the additional capability to provide band pass filtering of EEG signals.

26. The apparatus of claim 16 wherein the battery power supply is rechargeable.

27. A wireless system for EEG monitoring, comprising:
   a multiplicity of brain electrodes having conducting means to carry electrical signals to and from the multiplicity of brain electrodes;
   an EEG analysis workstation having the capability to process, store and display EEG signals from the multiplicity of brain electrodes, and further having the capability to identify epileptiform activity in the EEG signals;
   a workstation electronics module connected to the EEG analysis workstation, the workstation electronics module having the capability to provide bi-directional wireless data communication capability for the EEG analysis workstation;
   a patient electronics module comprising an interface to the conducting means carrying the EEG signals from the multiplicity of brain electrodes, a multiplicity of signal amplifiers having the capability to amplify the electrical signals carried by the conducting means from the multiplicity of brain electrodes, wherein the patient electronics module has the capability to send and receive data to and from the workstation electronics module.

28. The system of claim 27 wherein the EEG analysis workstation has the capability to automatically initiate electrical stimulation to the brain electrodes when epileptiform activity is detected.

29. The system of claim 27 wherein the EEG analysis workstation employs two or more detection algorithms that may be used concurrently to identify epileptiform activity.

30. The system of claim 27 wherein the patient electronics module further comprises an audio output jack for connecting an auditory stimulus device to the patient electronics module.

31. The system of claim 30 wherein the auditory stimulus device is a set of headphones.

32. The system of claim 30 wherein the auditory stimulus device is a loudspeaker.

33. The system of claim 27 wherein the patient electronics module further comprises an auxiliary stimulator interface for connecting additional stimulation devices to the patient electronics module.

34. The system of claim 27 wherein the wireless communication means uses radiofrequency electromagnetic wave signals.

35. The system of claim 27 wherein the wireless communication means uses infrared signals.

36. The system of claim 27 wherein the multi-channel amplifier has the additional capability to provide low pass filtering of EEG signals.

37. The system of claim 27 wherein the multi-channel amplifier has the additional capability to provide high pass filtering of EEG signals.

38. The system of claim 27 wherein the multi-channel amplifier has the additional capability to provide band pass filtering of EEG signals.

39. The system of claim 27 wherein the patient electronics module is battery powered.

40. The system of claim 27 wherein the patient electronics module further comprises analog-to-digital conversion circuitry capable of converting the outputs of the multiplicity of signal amplifiers into digitized EEG signals.

41. The system of claim 40 wherein the patient electronics module further comprises digital memory circuits capable of storing the digitized EEG signals for later transmission to the EEG analysis workstation.

42. The system of claim 41 wherein the digital memory has sufficient capacity to store 48 hours of EEG data from as many as 128 electrodes.

\* \* \* \* \*